(12) United States Patent
Schleipen et al.

(10) Patent No.: US 8,390,817 B2
(45) Date of Patent: Mar. 5, 2013

(54) EVANESCENT FIELD MODULATION IN A BIOSENSOR

(75) Inventors: Johannes Joseph Hubertina Barbara Schleipen, Eindhoven (NL); Dominique Maria Bruls, Eindhoven (NL); Josephus Arnoldus Hendricus Maria Kahlman, Tilburg (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 276 days.

(21) Appl. No.: 12/810,867

(22) PCT Filed: Dec. 18, 2008

(86) PCT No.: PCT/IB2008/055406
§ 371 (c)(1),
(2), (4) Date: Jun. 28, 2010

(87) PCT Pub. No.: WO2009/083879
PCT Pub. Date: Jul. 9, 2009

(65) Prior Publication Data
US 2010/0290052 A1    Nov. 18, 2010

(30) Foreign Application Priority Data
Jan. 3, 2008 (EP) .................................. 08100068

(51) Int. Cl.
G01N 21/55 (2006.01)
G01N 21/00 (2006.01)

(52) U.S. Cl. .................. 356/448; 356/432; 356/445

(58) Field of Classification Search ......... 356/445–448, 356/450–458
See application file for complete search history.

(56) References Cited

U.S. PATENT DOCUMENTS

| | | | | |
|---|---|---|---|---|
| 5,018,865 A | * | 5/1991 | Ferrell et al. | 356/600 |
| 5,637,458 A | * | 6/1997 | Frankel et al. | 435/6.12 |
| 5,939,709 A | * | 8/1999 | Ghislain et al. | 250/216 |
| 5,953,115 A | * | 9/1999 | Landers et al. | 356/237.2 |
| 6,883,559 B2 | * | 4/2005 | Jeon et al. | 141/9 |
| 7,123,764 B2 | | 10/2006 | Kirk et al. | |

FOREIGN PATENT DOCUMENTS

| | | |
|---|---|---|
| EP | 0635714 A1 | 1/1995 |
| JP | 2001264235 A | 9/2001 |
| JP | 2003035661 A | 2/2003 |
| WO | 0029820 A2 | 5/2000 |

OTHER PUBLICATIONS

Cohen: "Monolithic Chemical Sensor Using Heterodyned Sampled Grating DBR Lasers"; Electronic Letters, Oct. 25, 2001, vol. 37, No. 22 pp. 1358-1360.

(Continued)

*Primary Examiner* — Gregory J Toatley
*Assistant Examiner* — Jarreas C Underwood

(57) ABSTRACT

The present invention provides an FTIR system comprising a first light source emitting light of a first wavelength, a sample volume with an adjacent sensor surface, a detector for detecting light reflected at said sensor surface. The sensor surface is illuminated by said first light source fulfilling the condition of total internal reflection and generating an evanescent field with a decay length within the sample volume. The system further comprises means for changing the decay length of the evanescent field and means for correlating the detected signals with the change of the decay length of the evanescent field.

13 Claims, 6 Drawing Sheets

OTHER PUBLICATIONS

Siao, M. "Microfluidics: New Channels for Biological Research"; Harvard Science Review, Fall 2006, pp. 46-49.

Reilly et al: "Cancer Cell Chemotaxis in Microfluidic Devices"; Power Point Presentation, 2006, 19 Page Document.

Wang et al: "Differential Effects of EGF Gradient Profiles on MDA-MB-231 Breast Cancer Cell Chemotaxis"; Experimental Cell Research 300,(2004), pp. 180-189.

Walker et al: "Effects of Flow and Diffusion on Chemotaxis Studies in a Microfabricated Gradient Generator"; Lab Chip, Jun. 2005, vol. 5 (6), pp. 611-618.

Saadi et al: "A Parallel-Gradcient Microfluidic Chamber for Quantitative Analysis of Breast Cancer Cell Chemotaxis"; Biomed Microdevices (2006), vol. 8, pp. 109-118.

\* cited by examiner

EVANESCENT FIELD MODULATION IN A BIOSENSOR

FIELD OF THE INVENTION

The invention relates to a frustrated total internal reflection (FTIR) biosensor system and a method of detecting an FTIR biosensor signal.

BACKGROUND OF THE INVENTION

The Applicant has filed several co-pending applications relating to biosensors or biosensor systems. Biosensors usually allow for the detection of a given specific molecule within an analyte or fluid sample, wherein the amount of said molecule is typically small. Therefore, target particles, for example super-paramagnetic label beads, are used which bind to a specific binding site or spot only, if the molecules to be detected are present within the analyte or fluid sample. Alternatively, in an inhibition assay these molecules may inhibit the binding of these particles or beads to a sensor surface. One known technique to detect these label particles bound to the binding spots or binding surface is FTIR. Therein, light is coupled into the sample or sample volume at an angle at which total internal reflection can occur. If no particles are present close to the sample surface, the light is completely reflected. If, however, the label particles are bound to said surface, the condition of total internal reflection is violated, a portion of the light is scattered into the sample and thus the amount of light reflected by the surface is decreased. By measuring the intensity of the reflected light with an optical detector, it is possible to estimate the amount of particles or beads bound to the surface.

However, one drawback of FTIR is that FTIR systems work in such a way that the starting signal, i.e., the signal when no particles or beads are present close to the sensor surface, is high. Binding of beads to the surface will then decrease the initially high optical signal. Thus, the signal x of interest, namely the amount of beads close to the surface, is measured by way of (1-x), i.e., as a (small) change of an initially high or large signal. If the change of the signal x, is rather small compared to the total measured optical signal, i.e. (1-x), this may cause so-called "gain problems", as the starting signal is large with respect to the signal of interest. It is therefore difficult to amplify the signal x, as the background signal (1-x) is amplified as well, which may result, e.g., in a nonlinear behaviour or even a saturation of the amplifiers, ADC's etc. Furthermore, this leads to a signal which is very sensitive to gain variations and noise, e.g. electronic noise.

SUMMARY OF THE INVENTION

It would therefore be desirable to limit or at least to decrease the background in an FTIR biosensor system and to be able to measure the amount of beads bound to a sensor surface of such a biosensor in a direct way. It is therefore an object of the present invention to provide an improved FTIR biosensor system which overcomes the above-mentioned problems. It is a further object of the present invention to provide an improved method of performing an FTIR biosensor measurement or assay. These objects are achieved with the features of the claims.

The present invention is based on the idea to modulate the decay length of the evanescent field generated by FTIR and to demodulate the reflected signal accordingly. Thus, a "direct" signal is produced which vanishes once there are no particles present close to the sensor surface.

Accordingly, the present invention provides an FTIR system comprising a first light source emitting light of a first wavelength, a sample volume with an adjacent sensor surface, a detector for detecting light reflected at said sensor surface. The sensor surface is illuminated by said first light source fulfilling the condition of total internal reflection and generating an evanescent field with a decay length within the sample volume. The system further comprises means for changing the decay length of the evanescent field and means for correlating the detected signals with the change of the decay length of the evanescent field.

Several ways of changing the decay length of the evanescent field are conceivable. For example, the incidence angle, at which the sensor surface is being illuminated, may be varied in order to change the decay length of the evanescent field. It is, however, preferred that the means for changing the decay length of the evanescent field is adapted for varying the first wavelength of the first light source.

According to a preferred embodiment of the present invention, the FTIR system further comprises a second light source emitting light of a second wavelength different from the first wavelength and further comprises optics allowing for illuminating the sensor surface with the first and second light source. For example, the beams of the two light sources, e.g. a blue and a red laser, may be brought into overlap using dichroic mirrors. This allows for coupling red and blue light into the sample volume in a parallel manner.

It is preferred that the system further comprises a means for switching the first and second light source on and off in anti-phase. In case of a red and a blue laser, this means is preferably adapted to modulate both lasers with a high frequency, such as several 100 MHz, and to further modulate the wavelength with a moderate frequency between about 10 and 100 kHz. Since the light illuminating the sensor surface is reflected at said surface and detected by the detector, these intensity and wavelength modulations are detected. Said detected signal is then being demodulated by a means for demodulating. If the modulation frequency of the wavelength modulation has been chosen at sufficiently high frequencies, the 1/f noise present at low frequencies may be eliminated. Advantageously, this system further comprises a means for controlling the intensities of the first and second light sources with respect to each other.

The present invention also relates to a method of detecting an FTIR bio sensor signal. Said method comprises the step of illuminating a sensor surface adjacent to a sample volume with light of a first wavelength, wherein the condition of total internal reflection is fulfilled and an evanescent field with a decay length is generated within the sample volume. The method further comprises the steps of detecting the light reflected at the sensor surface and changing the decay length of the evanescent field during illumination and detection.

Therein, the decay length of the evanescent field may be changed by either varying the incidence angle of the illumination light beam or by varying the first wavelength.

Optionally the method further comprises the step of illuminating the sensor surface with light of a second wavelength. In that case, it is preferred that the sensor surface is illuminated alternately by light of the first and second wavelength. The method may also comprise the step of demodulating the detected signal.

These and other aspects of the invention will be apparent from and elucidated with reference to the embodiment(s) described hereinafter.

DETAILED DESCRIPTION OF EMBODIMENTS

Figure 1:
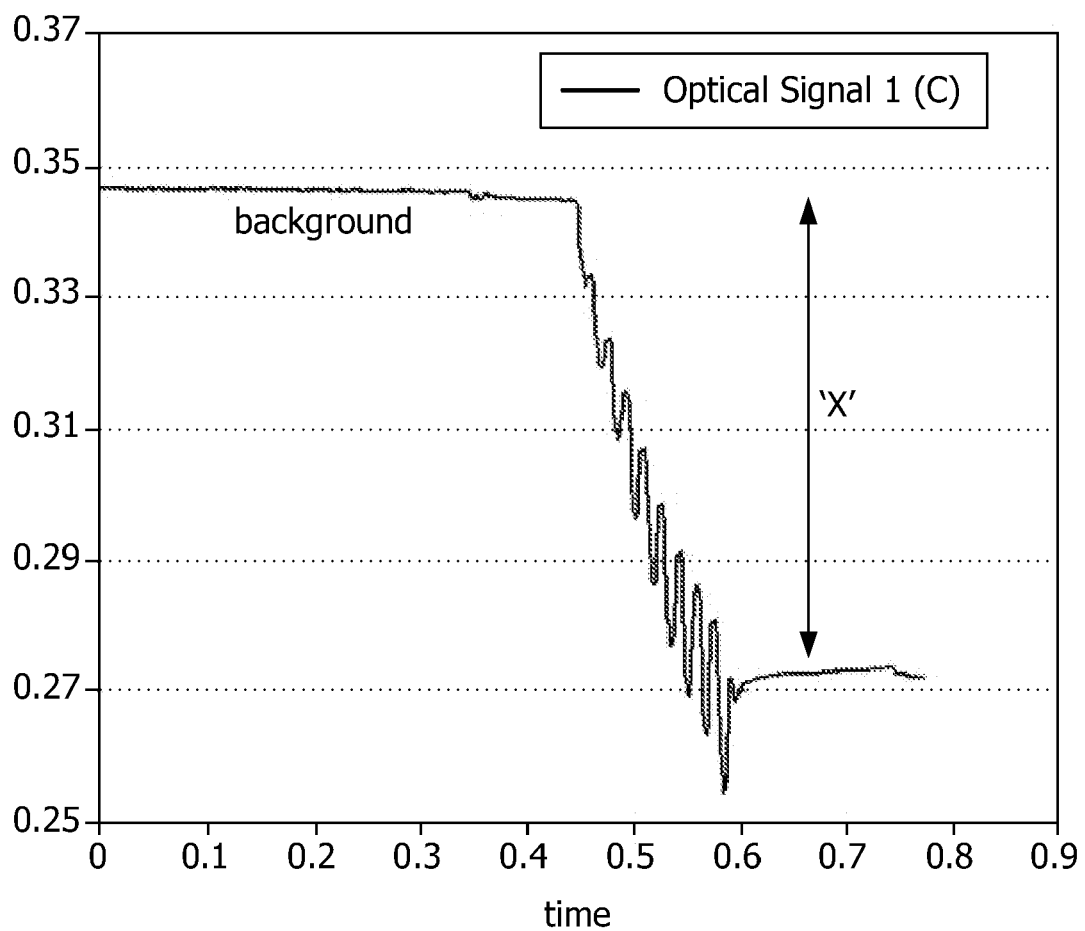
FIG. 1 schematically shows a detector signal of a prior art FTIR system.

FIG. 1 shows a diagram with a typical signal of a prior art FTIR system. The black curve represents the intensity of light being reflected at the sensor surface of the FTIR system. The units of intensity and time are arbitrary. At the beginning of the measurement, i.e. at t=0, the measured intensity starts at a value of about 0.35, which represents the background of said measurement. This is the amount of light being reflected at the sensor surface without any beads or particles present close to the sensor surface. After some time, i.e. at t=0.45, the particles precipitate or are forced, e.g. magnetically attracted, towards the sensor surface and consequently the intensity of the reflected light is reduced. The signal decreases down to a plateau of about 0.27, where the curve saturates or stabilizes. The oscillations in the signal in this case are due to the magnetic bead actuation protocol used in this particular type of assay.

The signal x of interest is the difference between this plateau and the background of 0.35 (indicated by the arrow). Thus, the actual information of interest amounts to a relative change of a signal of about 21%. In real assays the measured signal change can be as small 0.1%. This may, in general, lead to a bad signal-to-noise ratio and may, in particular, cause so-called gain problems. It is, for example, difficult to amplify a rather small signal x, as the background signal is then amplified as well, which may result in a saturation of the amplifiers. The present invention therefore aims at reducing or eliminating this background.

The present invention makes use of the fact that the decay length of the evanescent field decays exponentially in a direction perpendicular to the sensor surface. Accordingly, there is, in fact, only a very small layer above the sensor surface, which is sensitive to detecting particles. The present invention is based on the idea to actually change or vary, in particular, to modulate the decay length of the evanescent field. The decay length of the evanescent field may be calculated in the following manner:

$$z_{decay} = \frac{\lambda}{2\pi\sqrt{n_1^2\sin^2\theta - n_2^2}}$$

Therein, $\lambda$ is the wavelength of the light, $\theta$ is the angle of the incoming light with respect to the sensor surface normal, and $n_1$ and $n_2$ are the refractive indices of the substrate and the sample fluid, respectively. According to this formula, modulating the wavelength of the incoming light causes a modulation of the evanescent decay length of the probing optical field as well. This results in a modulated signal that can be detected using standard demodulation techniques.

Figure 2A:
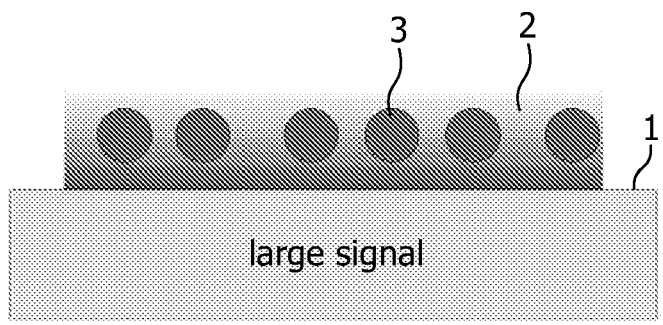
FIG. 2 schematically shows the dependence of the decay length of the evanescent field on the wavelength.
Figure 2B:
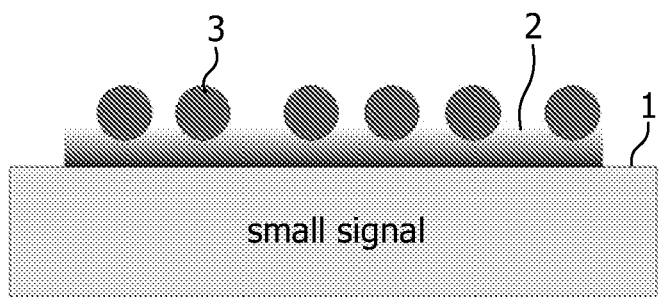

FIG. 2 schematically depicts the influence of the wavelength onto the decay length of the evanescent field. In FIG. 2a, a sensor surface 1 is illuminated with red light and generates an evanescent field 2 with a large decay length. Precipitated or bound particles 3 are fully immersed within the evanescent field 2 in this case. If blue light (i.e. smaller wavelength) is used instead of red light as in FIG. 2b, the decay length of the evanescent field 2 is significantly smaller and the particles 3 do only partly experience the evanescent field. Accordingly, switching between red and blue light leads to a different signal being reflected at the sensor surface.

Figure 3:
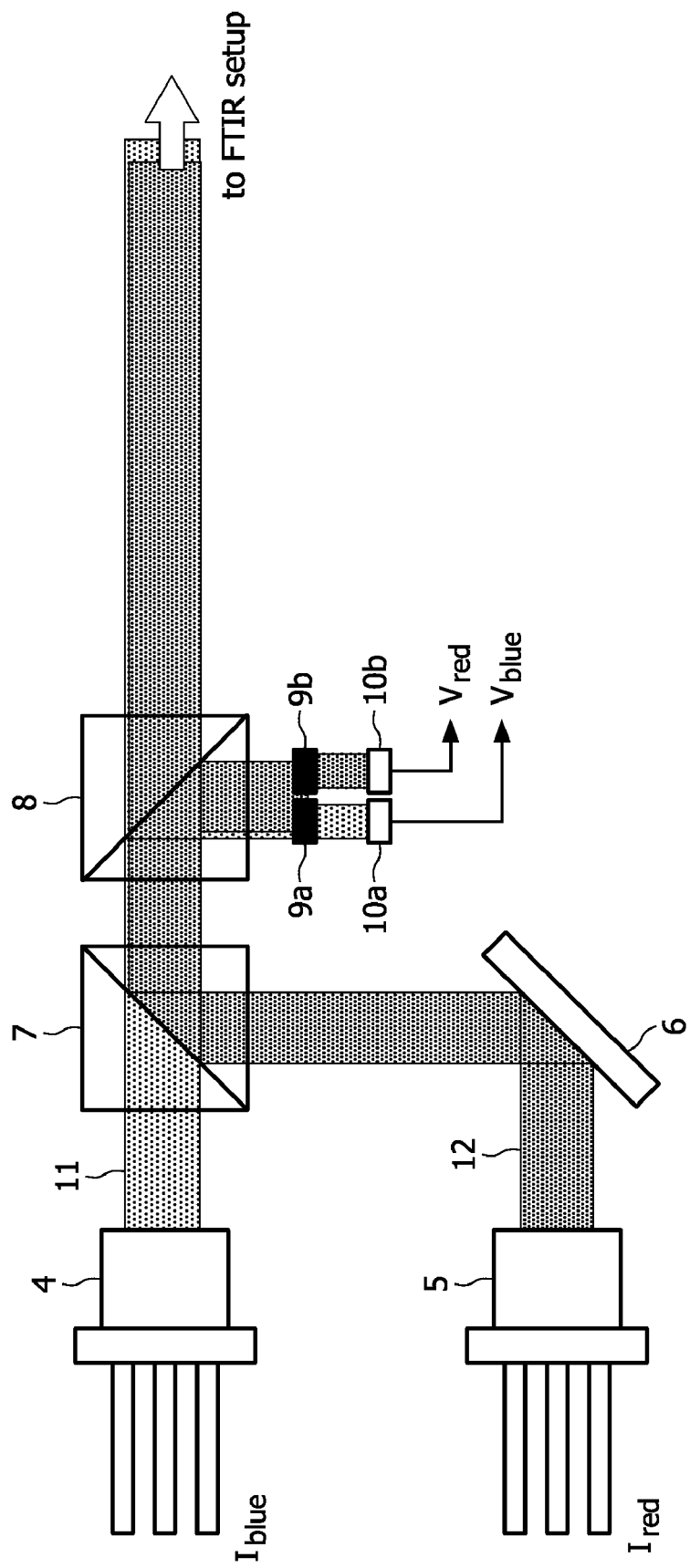
FIG. 3 schematically depicts a preferred embodiment of an FTIR system according to the present invention.

FIG. 3 shows a schematic diagram of an FTIR biosensor system according to a preferred embodiment of the present invention. A blue laser 4 and a red laser 5 generate blue and red light beams 11 and 12, respectively. The red light 12 is reflected at mirror 6 and coupled into dichroic mirror 7. Dichroic mirror 7 is used to create an overlap of beams 11 and 12. A second dichroic mirror 8 is used to couple a portion of the light beam out of the central beam. Said light is guided through color filters 9a and 9b onto detectors 10a and 10b for blue and red light, respectively. The central beam is used to illuminate the sensor surface of the sample volume.

Figure 4:
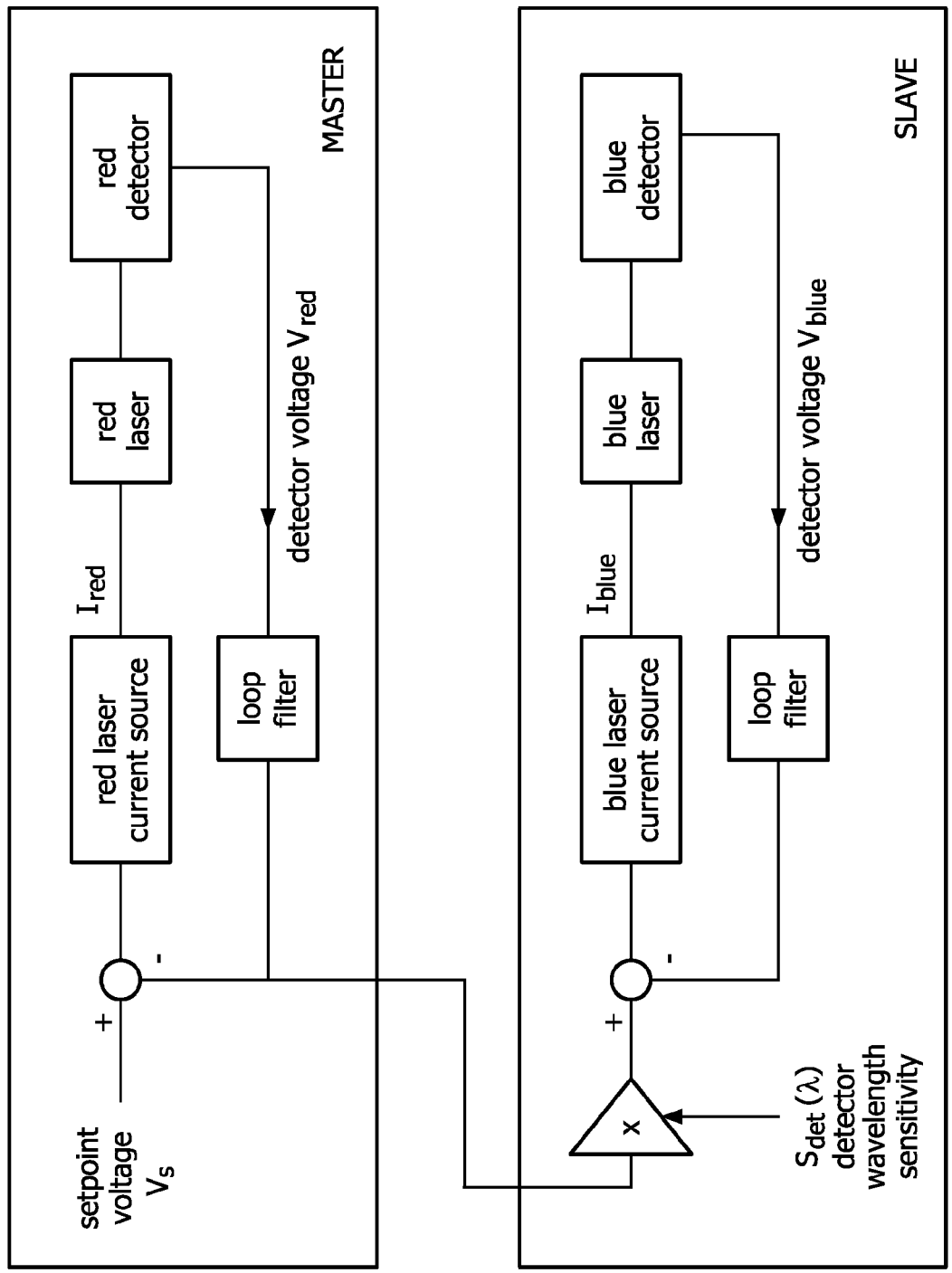
FIG. 4 shows in a block diagram how the light sources are controlled according to the present invention.

According to the present invention, the two laser sources 4 and 5 are switched on and off in anti-phase at a high frequency $f_\lambda$. The intensity of both laser beams 11 and 12 should be controlled in such a manner that the detector, which detects the light reflected at the sensor surface, shows identical response for both lasers if no beads or particles are present at the sensor surface. This can be accomplished, e.g., by a master-slave feedback control circuitry, as is illustrated in FIG. 4. A set-point voltage Vs is supplied to a red laser current source, which drives the red laser 5 (see FIG. 3). The red light is detected by red detector 10b, which outputs the detector voltage $V_{red}$. Said detector voltage $V_{red}$ is used to control the blue laser current source. However, in order to guarantee the above-mentioned identical response of the detectors for both laser beams, the detector voltage $V_{red}$ has to be modified, e.g. multiplied by a correction parameter, namely the detection wavelength sensitivity $S_{det}(\lambda)$. This parameter is suitably set taking the sensitivity of the detector for both wavelengths into account. Said control signal is supplied to a blue laser current source, which drives the blue laser 4. The intensity of the blue light is detected at blue detector 10a, which outputs a detector voltage $V_{blue}$ which is fed back to the blue laser current source. As can be seen in FIG. 4, the blue system is the slave of the red master. The red signal $V_{red}$ can be used as input for a first master control loop, trying to keep the optical output of the red laser at a constant value. At the same time, the actual measured detector voltage for the blue laser $V_{blue}$ is input into a second slave control loop, making the intensity of the blue laser equal to the intensity of the red laser. For this purpose, the detector sensitivity as a function of wavelength $S_{det}$ should be known. In general, this sensitivity is well known or can be measured.

Figure 5:
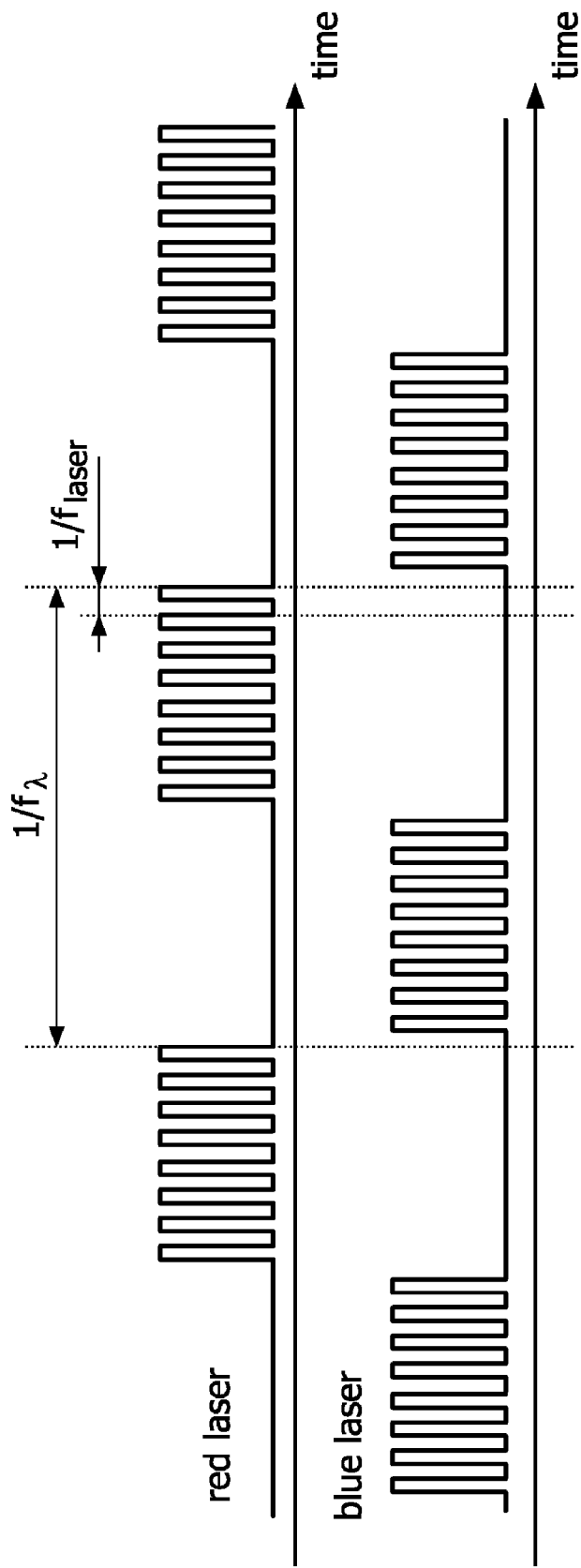
FIG. 5 shows the modulation scheme of two light sources according to the present invention.

FIG. 5 shows a modulation scheme using a red and a blue laser, that are readily available from optical storage technology. By modulating both lasers with a high frequency $f_{laser}$ (not shown) in the range of several 100 MHz, the laser output is stabilized and made insensitive for optical feedback. Furthermore, the wavelength of the incident beam is modulated by switching between the red and blue laser (not shown). As a wavelength modulation frequency $f_\lambda$ a frequency in the range of about 10-100 kHz is chosen. The signal originating from beads or particles located close to the sensor surface may then be detected by either directly demodulating at the modulation frequency $f_\lambda$ or by demodulating at the side band frequencies $f_{laser} \pm f_\lambda$.

If $f_\lambda$ is chosen at a sufficiently high frequency, the 1/f noise present at low frequencies is eliminated. Furthermore, if both laser powers are properly calibrated using the above-mentioned control loop, there will be no frequency components in this detector signal at $f_\lambda$ or at $f_{laser} \pm f_\lambda$. Accordingly, no signal is measured if no beads or particles are present. Here it is assumed that both frequencies, $f_{laser}$ and $f_\lambda$, are well above the control loop filter bandwidth $f_{LF}$. The bandwidth of the control loop filter is chosen such that low frequency signal variations, e.g. drift due to temperature variations, can be eliminated during the measurement procedure.

As soon as particles are bound to the sensor surface, a signal with frequency $f_\lambda$ is generated. The intensity of the signal is linearly dependent on the amount of particles. The signal will, in general, not be linearly dependent on the wavelength. However, the used wavelengths are fixed and well known, which results in an instrumental calibration factor that is constant during the measurements.

In the embodiment described above, the signal is retrieved by demodulation.

According to a further preferred embodiment of the present invention, a real DC-free measurement can be obtained in the following manner. Both lasers are pulsed in anti-phase with a frequency $f_\lambda$ as already described above. The control loops for stabilizing the output powers of the two lasers can also be controlled by the main detector, which detects the light reflected at the sensor surface. For this purpose, the main detector should be sampled synchronously with the laser modulation scheme. For example, the even pulses could measure the reflection of red light, whereas the odd pulses could measure the reflection of blue light. Alternatively, one could use two discrete detectors in combination with two color filters.

The signal containing the information about the particles or beads present at the sensor surface is now defined as the difference signal between the reflection of red light and the reflection of blue light. In order to get rid of all offsets prior to the start of the actual measurement, the second control loop governing the output of the blue laser uses this difference signal as its control signal. Accordingly, the intensity of the blue laser is controlled such that all offsets are reduced to zero automatically. As soon as the sample fluid is introduced into the sample volume and the actual measurement starts, the second control loop is interrupted and its latest sampled control signal is put on hold and used as static control for the blue laser current source. As soon as particles start to penetrate the evanescent wave, the difference signal between red and blue reflection will deviate from zero, since the red laser will show stronger scattering compared to the blue laser. In this case, a real zero signal base line can be measured.

Figure 6A:
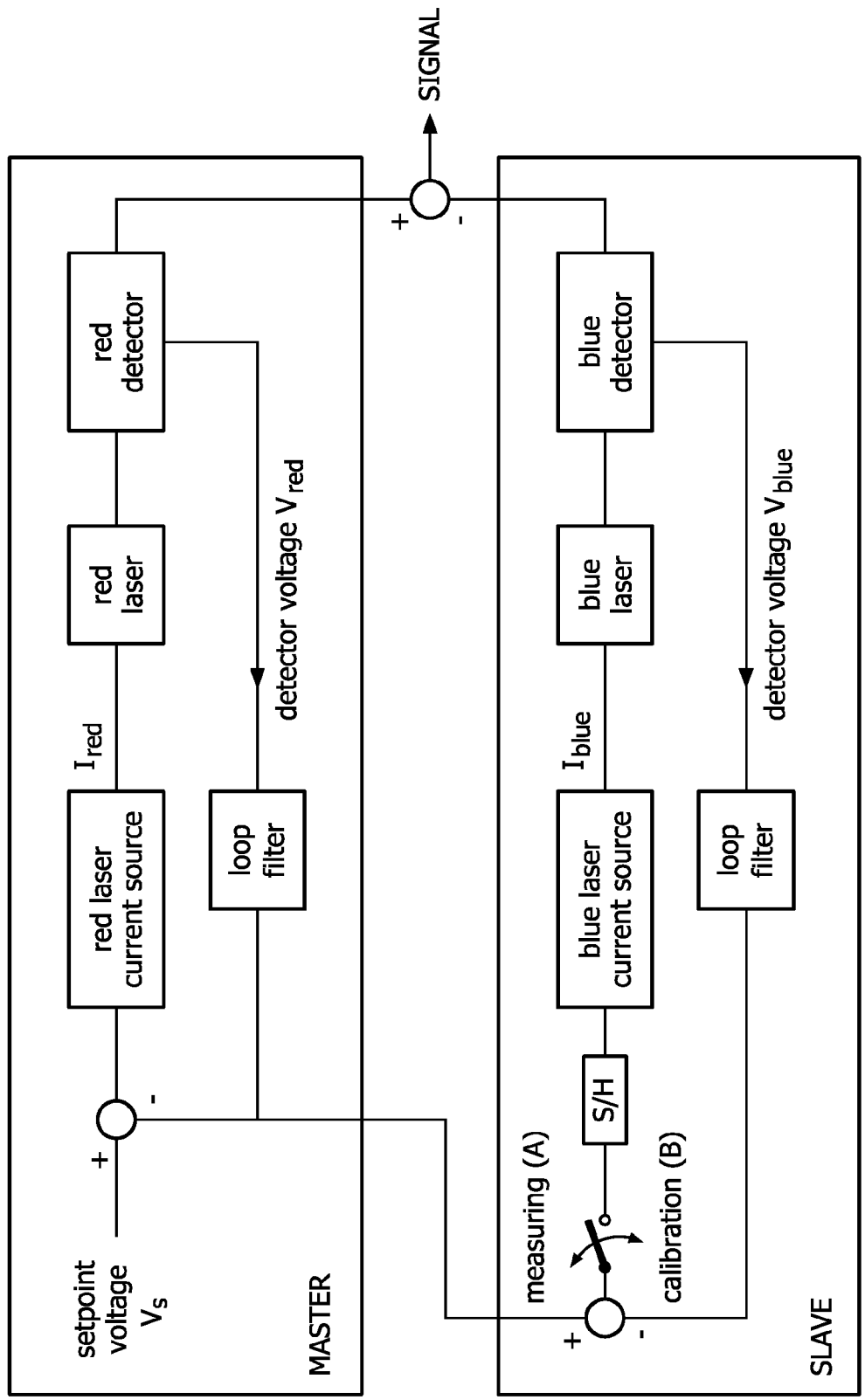
FIG. 6a shows another block diagram of how to control the two light sources according to the present invention.
Figure 6B:
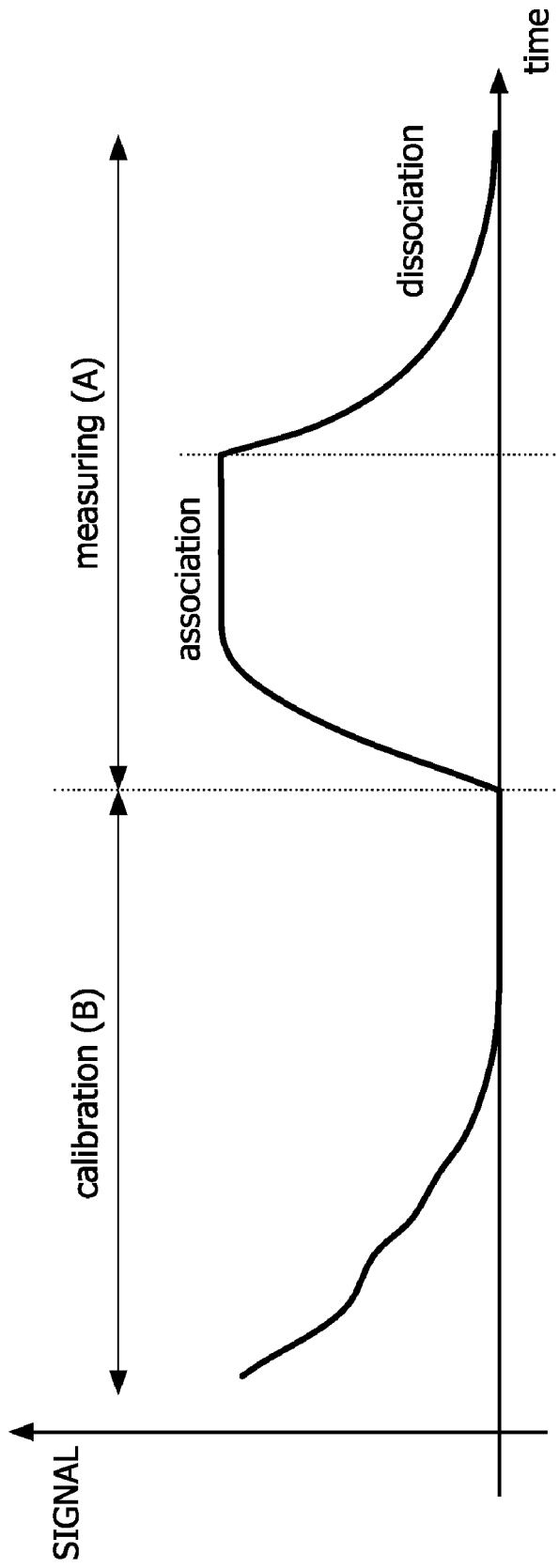
FIG. 6b schematically shows a detector signal of an FTIR system according to the present invention.

FIG. 6 shows the respective control loop for this embodiment. FIG. 6b depicts a typical detector output for this embodiment. At the beginning of the measurement a calibration step takes place as described above until the signal is minimized. Once this zero signal base line is established, particles may be forced towards the sensor surface leading to an increase in a real or direct signal.

According to a further embodiment, modulation of the decay length of the evanescent field is achieved by modulating the incidence angle of the illuminating light beam with respect to the normal of the sensor surface. In general, a larger entrance angle with respect to the normal of the sensor surface will result in a smaller evanescent decay length. Accordingly, varying the incidence angle and demodulating the signal reflected at the sensor surface will lead to a "direct" signal as well, which is only dependent on the amount of particles close to the sensor surface.

Of course, one has to make sure, that the incidence angle as used always fulfills the condition of total internal reflection.

The variation of the incidence angle may be achieved by, e.g., moving the light source and the detector in perfect anti-phase in order to make sure that the reflected light will always be focused on the detector.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

The invention claimed is:

1. FTIR system comprising a first light source emitting light of a first wavelength, a sample volume with an adjacent sensor surface, wherein the sensor surface is illuminated by said first light source fulfilling the condition of total internal reflection and generating an evanescent field with a decay length within the sample volume, a detector for detecting light reflected at the sensor surface, means for changing the decay length of the evanescent field, and means for correlating the detected signals with the change of the decay length of the evanescent field.

2. System according to claim 1, wherein the means for changing the decay length is adapted for varying the first wavelength of the first light source.

3. System according to claim 1, further comprising a second light source emitting light of a second wavelength different from the first wavelength and optical means allowing for illuminating the sensor surface with the first and second light source.

4. System according to claim 3, further comprising a means for switching the first and second light source on and off in anti-phase.

5. System according to claim 1, further comprising a means for demodulating the signal detected by the detector.

6. System according to claim 5, further comprising a means for controlling the intensities of the light beams of the first and second light sources with respect to each other.

7. System according to claim 1, wherein the means for changing the decay length is adapted for varying the angle between the sensor surface and the light beams of the first light source.

8. Method of detecting an FTIR bio sensor signal comprising the following steps:
   a) illuminating a sensor surface adjacent to a sample volume with light of a first wavelength, wherein the condition of total internal reflection is fulfilled and an evanescent field with a decay length is generated within the sample volume;
   b) detecting the light reflected at the sensor surface;
   c) changing the decay length of the evanescent field during steps a) and b); and
   d) correlating the detected signal with the change of the decay length of the evanescent field.

9. Method according to claim 8, wherein the decay length of the evanescent field is changed by varying the first wavelength.

10. Method according to claim 8, further comprising the step of illuminating the sensor surface with light of a second wavelength.

11. Method according to claim 10, wherein the sensor surface is illuminated alternately by light of the first and second wavelength.

12. Method according to claim 8, further comprising the step of demodulating the detected signal.

13. Method according to claim 8, wherein the decay length of the evanescent field is changed by varying the entrance angle of the illumination.

* * * * *